US008784822B2

(12) United States Patent
Skurkovich et al.

(10) Patent No.: US 8,784,822 B2
(45) **Date of Patent: *Jul. 22, 2014**

(54) METHOD AND COMPOSITION FOR TREATMENT OF RENAL FAILURE WITH ANTIBODIES AND THEIR EQUIVALENTS AS PARTIAL OR COMPLETE REPLACEMENT FOR DIALYSIS

(76) Inventors: Boris Skurkovich, Pawtucket, RI (US); Ellen Millstein, LaJolla, CA (US); Simon Skurkovich, Rockville, MD (US)

( * ) Notice: Subject to any disclaimer, the term of this patent is extended or adjusted under 35 U.S.C. 154(b) by 935 days.

This patent is subject to a terminal disclaimer.

(21) Appl. No.: 12/367,643

(22) Filed: Feb. 9, 2009

(65) Prior Publication Data

US 2009/0148446 A1 Jun. 11, 2009

Related U.S. Application Data

(63) Continuation of application No. 11/375,378, filed on Mar. 14, 2006, now Pat. No. 7,504,106.

(51) Int. Cl.
*A61K 39/395* (2006.01)
*A61K 38/00* (2006.01)

(52) U.S. Cl.
USPC .................... 424/158.1; 424/130.1; 514/15.4; 514/1.1

(58) Field of Classification Search
None
See application file for complete search history.

(56) References Cited

U.S. PATENT DOCUMENTS

| | | | | |
|---|---|---|---|---|
| 3,773,919 | A | 11/1973 | Boswell et al. | |
| 4,485,177 | A | 11/1984 | Siedel et al. | |
| 4,578,361 | A | 3/1986 | Siedel et al. | |
| 4,816,567 | A | 3/1989 | Cabilly et al. | |
| 5,395,760 | A | 3/1995 | Smith et al. | |
| 5,451,658 | A | 9/1995 | Seelig | |
| 5,578,707 | A | 11/1996 | Novick et al. | |
| 5,605,690 | A | 2/1997 | Jacobs et al. | |
| 5,759,808 | A | 6/1998 | Casterman et al. | |
| 5,800,988 | A | 9/1998 | Casterman et al. | |
| 5,840,526 | A | 11/1998 | Casterman et al. | |
| 5,945,397 | A | 8/1999 | Smith et al. | |
| 6,015,695 | A | 1/2000 | Casterman et al. | |
| 6,080,557 | A * | 6/2000 | Sims et al. | 435/69.1 |
| 6,201,105 | B1 | 3/2001 | Smith et al. | |
| 6,333,032 | B1 | 12/2001 | Skurkovich et al. | |
| 6,335,163 | B1 | 1/2002 | Sharon | |
| 6,572,852 | B2 | 6/2003 | Smith et al. | |
| 2003/0049255 | A1 | 3/2003 | Sims et al. | |

FOREIGN PATENT DOCUMENTS

| | | | |
|---|---|---|---|
| DE | 19845286 | A1 | 4/2000 |
| WO | 93/17715 | A1 | 9/1993 |
| WO | 2004/061104 | A2 | 7/2004 |
| WO | 2005/042774 | A2 | 5/2005 |

OTHER PUBLICATIONS www.mayoclinic.com/health/glomerulonephritis, downloaded Feb. 15, 2010.*

Couser. 1999. Lancet 353:1509-15.*

International Search Report, mailed Nov. 15, 2007, from International Application No. PCT/US2007/063877, filed on Mar. 13, 2007.

Written Opinion of the International Searching Authority from International Application No. PCT/US2007/063877, filed on Mar. 13, 2007.

A-Z Heatlh Guide from WebMD: Health Topics: Chronic Kidney Disease, Exams and Tests, http://www.webmd.com/hw/kidney__failure/aa65440.asp?pagenumber=2, downloaded Sep. 11, 2006.

A-Z Heatlh Guide from WebMD: Health Topics: Chronic Kidney Disease, What Happens, http://www.webmd.com/hw/kidney__failure/aa65434.asp?pagenumber=2, downloaded Sep. 11, 2006.

About.com: Arthritis, arthritis.about.com/od/enbrel/p/enbrelfacts.htm?p=1, downloaded Jan. 29, 2008.

Benkert, A., et al., "Development of a Creatinine Elisa and an Amperometric Antibody-Based Creatinine Sensor with a Detection Limit in the Namomolar Range," Analytical Chemistry, vol. 72, No. 5, Mar. 1, 2000, pp. 916-921.

Bird, R. E., et al., "Single-Chain Antigen-Binding Proteins," Science, vol. 242, Oct. 21, 1988, pp. 423-426.

Carracedo, J., et al., "Monocytes from dialysis patients exhibit characteristics of senescent cells: does it really mean inflammation?" Contrib Nephrol, vol. 149, 2005, pp. 208-218, Abstract.

Clackson, T., et al., "Making antibody fragments using phage display libraries," Nature, vol. 352, Aug. 15, 1991, pp. 624-628.

Cooper, A. C., et al., "Increased Expression of Erythropoiesis Inhibiting Cytokines (IFN-γ, TNF-α, IL-10, and IL-13) by T Cells in Patients Exhibiting a Poor Response to Erythropoietin Therapy," J. Am. Soc. Nephrol, vol. 14, 2003, pp. 1776-1784.

(Continued)

*Primary Examiner* — Shulamith H Shafer
(74) *Attorney, Agent, or Firm* — Houston & Associates, LLP

(57) ABSTRACT

A method for treating renal failure associated with advanced stage renal disease includes administering a soluble cytokine receptor to one or more of tumor necrosis factor alpha, interferon gamma or interleukin 6; or antibodies to one or more of interleukin 6 or interleukin 1 beta. The method can be used as a supplement to or as partial or complete replacement for dialysis. A pharmaceutical composition includes antibody or functional equivalent thereof to urea, creatinine, or both; antibody, functional equivalent or soluble cytokine receptor to tumor necrosis factor alpha, interferon gamma, interleukin 6, interleukin 1 beta or any combination thereof. The composition can be included in a kit.

4 Claims, No Drawings

(56) References Cited

OTHER PUBLICATIONS

De Stgroth, S. F., et al., "Production of monoclonal antibodies: strategy and tactics," J. Immunol Methods, 1980, vol. 35, No. 1-2, pp. 1-21, Abstract.
De Vriese, A. S., et al., "Can inflammatory cytokines be removed efficiently by continuous renal replacement therapies?" Intensive Care Med,1999, vol. 25, pp. 903-910.
Fisher, C. J., Jr., et al, "Treatment of Septic Shock with the Tumor Necrosis Factor Receptor:Fc Fusion Protein," The New England Journal of Medicine, vol. 334, No. 26, Jun. 27, 1996, pp. 1697-1702.
Galli, F. et al., "Glycoxidation and inflammatory markers in patients on treatment with PMMA-based protein-leaking dialyzers," Kidney International, vol. 67, 2005, pp. 750-759.
Glomerulonephritis, www.healthsystem.virgina.edu/uvahealth/peds_urology/glomerul.cfm, modified Feb. 12, 2004, downloaded Aug. 21, 2007.
Gringeri, A., et al., "Absence of Clinical, Virological, and Immunological Signs of Progression in HIV-1-Infected Patients Receiving Active Anti-Interferon-[alpha] Immunization: A 30-Month Follow-Up report," Journal of Acquired Immune Deficienty Syndrome, vol. 13, No. 1, Sep. 1996, pp. 55-67.
Gringeri, A., et al., "A randomized, placebo-controlled, blind anti-AIDS clinical trial: safety and immunogenicity of a specific anti-IFN alpha immunization," Journal of Acquired Immune Deficienty Syndrome, Sep. 1994, vol. 7, No. 9, pp. 978-988, Abstract.
Guyton et al., "Textbook of Medical Physiology," 11th Edition, 2006, Chapter 31, pp. 402-415.
Hamers-Casterman, C., et al., "Naturally occurring antibodies devoid of light chains," Nature, vol. 363, Jun. 3, 1993, pp. 446-448.
Han, S. et al., "Effect of anti-tumor necrosis factor-alpha monoclonal antibody in alleviating renal ischemia-reperfusion injury," Academic Journal of the First Medical College of PLA, vol. 23, No. 4, 2003, pp. 332-334, Abstract.
Harrison's Principles of Internal Medicine 16th Edition, Part II, Chapter 262, "Dialysis in the Treatment of Renal Failure," Jul. 23, 2004, Abstract.
Hassan, K., et al., "Effect of erythropoietin therapy on red cells filterability and left ventricular mass in predialysis patients," Ren. Fail., 2005, vol. 27, No. 2, pp. 77-82, Abstract.
Haurum, J., et al., "Recombinant polyclonal antibodies: Therapeutic antibody technologies come full circle," IDrugs, 2005, vol. 8, No. 5, pp. 404-409.
Himmelfarb, J., et al., "Imparied monocyte cytokine production in critically ill patients with acute renal failure," Kidney International, vol. 66, 2004, pp. 2354-2360.
Huston, J. S., et al., "Protein engineering of antibody binding sites: Recovery of specific activity in an anti-digoxin single-chain Fv analogue produced in *Escherichia coli,*" Proc. Natl. Acad. Sci, vol. 85, Aug. 1988, pp. 5879-5883.
Jacobs, P., et al., "Interleukin/cytokine profiles in haemodialysis and in continuous peritoneal dialysis," Nephrol Dial Transplant, 2004, vol. 19 [Suppl 5], pp. 41-45.
Jones, P. T., et al., "Replacing the complementarity-determining regions in a human antibody with those from a mouse," Nature, vol. 321, May 29, 1986, pp. 522-525.
Kaysen, G. A., "The microinflammatory state in uremia: causes and potential consequences," Journal of the American Society of Nephrology, vol. 12, No. 7, Jul. 2001, pp. 1549-1557, Abstract.
Kaysen, G. A., et al., "Characteristics and Effects of Inflammation in End-Stage Renal Disease," Seminars in Dialysis, vol. 16, No. 6, 2003, pp. 438-446.
Khan, S. B. et al., "Antibody blockade of TNF-alpha reduces inflammation and scarring in experimental crescentic glomerulonephritis," Kidney International, vol. 67, No. 5, 2005, pp. 1812-1820.
Kierdorf, H. P., et al., "Cytokines and chronic renal replacement measures," Internist (Berl), Jan. 2001, vol. 42, No. 1, pp. 86-91, Abstract.
Killard, A. J., et al., "Creatinine biosensors: principles and designs," Trends in Biotechnology, vol. 18, No. 10, 2000, pp. 433-437.
Kleinert, J. et al., "Refractory Wegener's granulomatosis responds to tumor necrosis factor blockade," Weiner Klinische Wochenschau, vol. 116, No. 9-10, 2004, pp. 334-338.
Kodadek, T., et al., "Synthetic Molecules as Antibody Replacements," Accounts of Chemical Research, vol. 37, No. 9, 2004, pp. 711-718.
Kohler & Millstein, "Continuous cultures of fused cells secreting antibody of predefined specificity," Nature, vol. 256, Aug. 7, 1975, pp. 495-497.
Kostelny, S. A., et al., "Formation of a Bispecific Antibody by the Use of Leucine Zippers," The Journal of Immunology, vol. 148, No. 5, Mar. 1, 1992, pp. 1547-1553.
Krause, I., et al., "Autoimmune Aspects of Cytokine and Anticytokine Therapies," Am. J. Med., 2003, vol. 115, pp. 390-397.
Lutz, Y., et al., "The distribution of two hnRNP-associated proteins defined by a monoclonal antibody is altered in heat-shocked HeLa cells," Experimental Cell Research, vol. 175, Issue 1, Mar. 1988, pp. 109-124, Abstract.
MacDougall, I. C., "Could anti-inflammatory cytokine therapy improve poor treatment outcomes in dialysis patients?" Nephrol Dial Transplant, 2004, 19 [Suppl 5], pp. 73-78.
Marks, J. D., et al., "By-passing immunization, Human antibodies from V-gene libraries displayed on phage," Journal of Molecular Biology, vol. 222, Issue 3, Dec. 5, 1991, pp. 581-597, Abstract.
Martikainen, T. A., et al., Cytokines and Other Soluble Factors in Dialysate—Indicators of Altered Peritoneal Function? Scandinavian Journal of Urology and Nephrology, vol. 36, No. 6, Dec. 30, 2002, pp. 450-454(5), Abstract.
Maruyama Y., et al., "Role of Interleukin-1beta in the Development of Malnutrition in Chronic Renal Failure Patients," Blood Purif., May 30, 2005, vol. 23, No. 4, pp. 275-281 [Epub ahead of print], Abstract.
Matsumoto, K., et al., "Cytokine," Nippon Rinsho, Jun. 2004, vol. 62 Suppl. 6, pp. 215-219, Abstract.
Medical Encyclopedia: Chronic glomerulonephritis, www.nlm.nih.gov/medlineplus/ency/article/000499.htm, updated Sep. 13, 2005, downloaded Aug. 21, 2007.
Medical Encyclopedia: Glomerulonephritis, www.nlm.nih.gov/medlineplus/ency/article/000484.htm, updated Sep. 13, 2005, downloaded Mar. 25, 2007.
Memoli, B., et al., "The IL-6 soluble receptors in hemodialyzed patients," G. Ital Nefrol, Nov.-Dec. 2004, vol. 21, Suppl 30, pp. S117-S121, Abstract.
Milstein, C., et al., "Hybrid hybridomas and their use in immunohistochemistry," Nature, vol. 305, Oct. 6, 1983, pp. 537-540.
Montero-Julian, F. A., et al., "Pharmacokinetic Study of Anti-Interleukin-6 Therapy With Monoclonal Antibodies: Enhancement of IL-6 Clearance by Cocktails of Anti-IL-6 Antibodies," Blood, vol. 85, No. 4, Feb. 15, 1995, pp. 917-924.
Morgera, S., et al., "Renal replacement therapy with high-cutoff hemofilters; Impact of convection and diffusion on cytokine clearances and protein status," Am J. Kidney Dis., Mar. 2004, vol. 43, No. 3, pp. 444-453, Abstract.
Morrison, S. L., et al., "Chimeric human antibody molecules: Mouse antigen-binding domains with human constant region domains," Proc. Natl. Acad. Sci, vol. 81, Nov. 1984, pp. 6851-6855.
Obrador, G. T., et al., "Epidemiology of chronic kidney disease and screening recommendations," UpToDate: Epidemiology of chronic kidney disease and screening recommendations, http://www.uptodate.com/patients/content/topic.do?topicKey=~vt3vNCTO/CaJut, updated Oct. 1, 2008, downloaded Jan. 23, 2009.
Panichi, V., et al., "C-Reactive Protein and Interleukin-6 Levels are Related to Renal Function in Predialytic Chronic Renal Failure," Nephron Journals, vol. 91, No. 4, 2002, Abstract.
Pereira, B. J., "Cytokine production in patients on dialysis," Blood Purif., 1995, vol. 13, No. 3-4, pp. 135-146, Abstract.
Pertosa G., et al., "Clinical relevance of cytokine production in hemodialysis," Kidney Int. Suppl., Aug. 2000, vol. 76, pp. S104-S111, Abstract.
Presta, L., "Antibody engineering for therapeutics," Current Opinion in Structural Biology, 2003, vol. 13, pp. 519-525.
Riechmann, L., et al., "Reshaping human antibodies for therapy," Nature, vol. 332, Mar. 24, 1988, pp. 323-327.

(56) References Cited

OTHER PUBLICATIONS

Rohde, M., et al., "Production and Characterization of Monoclonal Antibodies Against Urea Derivatives," Applied Biochemistry and Biotechnology, vol. 75, No. 1, 1998, pp. 129-137.
Rudikoff, S., et al., "Single amino acid substitution altering antigen-binding specificity," Proc. Natl. Acad. Sci., vol. 79, Mar. 1982, pp. 1979-1983.
Shlipak, M. G., et al, "Elevations of Inflammatory and Procoagulant Biomarkers in Elderly Persons With Renal Insufficiency," Circulation, Jan. 2003, pp. 87-92.
Sitter T., et al., "Dialysate related cytokine induction and response to recombinant human erythropoietin in haemodialysis patients," Nephrology Dialysis Transplantation, vol. 15, No. 8, Aug. 2000, pp. 1207-1211, Abstract.
Standiford, T. J., "Anti-inflammatory Cytokines and Cytokine Antagonists," Current Pharmaceutical Design, 2000, vol. 6, pp. 633-649.
Stenvinkel, P., et al., "Inflammation in end-stage renal disease: sources, consequences, and therapy," Semin Dial, Sep.-Oct. 2002, vol. 15, No. 5, pp. 329-337, Abstract.
Stenvinkel, P., et al., "IL-10, IL-6, and TNF-$\alpha$: Central factors in the altered cytokine network of uremia—The good, the bad, and the ugly," Kidney International, vol. 67, 2005, pp. 1216-1233.
Symons, J. A., et al., "Soluble type II interleukin 1 (IL-1) receptor binds and blocks processing of IL-1$\beta$ precursor and loses affinity for IL-1 receptor antagonist," Proc. Natl. Acad. Sci., vol. 92, Feb. 1995, pp. 1714-1718.
Teraoka, S., et al., "Can Cytokines be Removed by Hemofiltration of Hemoadsorption?" ASAIO J., vol. 46, No. 4, Jul./Aug. 2000, pp. 448-451.
Tetta, C., et al., "Alterations of the cytokine network in hemodialysis," J. Nephrol, Nov.-Dec. 2001, vol. 14 Suppl 4, pp. S22-S29, Abstract.
Tripepi, G., et al., "Inflammation markers, adhesion molecules, and all-cause and cardiovascular mortality in patients with ESRD: searching for the best risk marker by multivariate modeling," J Am Soc Nephrol, Mar. 2005, vol. 16 Suppl 1, pp. S83-S88.
Uchino, S., et al., "Cytokine Dialysis: An Ex Vivo Study," ASAIO J., vol. 48, No. 6, Nov./Dec. 2002, pp. 650-653.
Waterston, A. M., et al., "Phase I study of TNF alpha AutoVacclne in Patients with metastic cancer," Cancer Immunol Immunother, 2005, vol. 54, pp. 848-857.
Weir, A. N., et al., "Formatting antibody fragments to mediate specific therapeutic functions," Biochemical Society Transactions, 2002, vol. 30, part 4, pp. 512-517.
Yao, Q., et al., "Chronic Systemic Inflammation in Dialysis Patients: An Update on Causes and Consequences," ASAIO Journal, vol. 50, No. 6, Nov./Dec. 2004, pp. LVII-LVII.

* cited by examiner

METHOD AND COMPOSITION FOR TREATMENT OF RENAL FAILURE WITH ANTIBODIES AND THEIR EQUIVALENTS AS PARTIAL OR COMPLETE REPLACEMENT FOR DIALYSIS

RELATED APPLICATIONS

This application is a Continuation of U.S. Pat. No. 7,504,106, issued on Mar. 17, 2009, which is incorporated herein by reference in its entirety.

BACKGROUND OF THE INVENTION

Chronic renal disease is a world-wide problem. In the United States, there were over 400,000 patients enrolled in Medicare-funded end-stage renal disease programs at the end of 2002. It is projected that by 2010, more than 650,000 patients will be enrolled in such programs, at a cost of over $28 billion a year. In spite of improvements in dialysis therapy, patients often experience a decline in quality of life. Mortality and morbidity continue to be significant.

Renal failure is associated with an inability of the kidneys to excrete large loads of electrolytes and other substances. As a result, patients often experience generalized edema, acidosis, high concentration of non-protein nitrogen compounds, especially urea, and high concentrations of other urinary retention products including creatinine. This condition is known as uremia.

Chronic kidney disease also is associated with the malnutrition, inflammation and atherosclerosis (MIA) syndrome. In fact, atherosclerotic cardiovascular disease is a leading cause of morbidity and mortality in end-stage renal disease (ESRD) patients. In many cases, ESRD patients also do not respond to erythropoietin therapy employed to manage their anemia.

It is well established that ESRD is a state of chronic systemic inflammation. The kidney is an organ that not only excretes cytokine metabolites but also contributes to cytokine production through its endocrinal function. It has been reported that the kidney may play a role in handling the clearance of pro-inflammatory cytokines. Even mild to moderate reduction in glomerular filtration rate appears to result in increased levels of circulating pro-inflammatory cytokines.

The hemodialysis procedure itself contributes to an inflammatory response and mortality in dialysis patients is higher than that in the general population across all age groups. Hemodialysis patients suffer from chronic inflammation for reasons such as potential blood contamination from endotoxin in the dialysis fluid, repeated contact of blood with artificial materials in the extracorporeal circuit, infections related to vascular access problems and so forth.

An approach for the non-specific elimination of circulating cytokines by continuous renal replacement therapies (CRRT) was proposed but reported controversial. In addition, it was found that treatment with oral pentoxyfilline could reduce T-cell expression of TNF-α and IFN-γ. The use of steroids, thalidomide, anti-thymocyte globulin, anti-lymphocyte globulin and of the anti-CD3 monoclonal antibody OKT3 has been suggested. Inhibitors of TNF-α have been approved by the U.S. FDA as therapies for patients with various autoimmune diseases including rheumatoid arthritis, ankylosing spondylitis, psoriasis and psoriatic arthritis and Crohn's disease; their use in systemic inflammatory response syndrome (SIRS) and for reversing the inflammatory process in erythropoietic resistance has been suggested. IL-1 receptor antagonist has been approved by U.S. FDA to treat rheumatoid arthritis and anti-IL-6 receptor antibody has been tested in patients with rheumatoid arthritis with good results. In addition, a humanized monoclonal antibody to IFN-γ is now in clinical testing for the treatment of Crohn's disease.

SUMMARY OF THE INVENTION

A need continues to exist, therefore, for methods of treating renal disease and in particular for treatments that can be provided in conjunction with or as a replacement for renal or peritoneal dialysis.

Generally the invention relates to a method and composition for treating renal disease. In further aspects, the invention relates to a process for making the composition and to a kit suitable in administering the treatment.

The treatment disclosed herein can be administered as a supplement to dialysis or as partial or complete replacement of dialysis. In some patients, the treatment can be used to delay the onset of kidney failure.

In one embodiment of the invention a method for treating renal disease includes selecting a patient suffering from renal disease and administering to the patient an antibody component, wherein a first portion of the antibody component is to a compound selected from the group consisting of urea, creatinine and any combination thereof, and wherein a second portion of the antibody component is to a cytokine selected from the group consisting of tumor necrosis factor alpha, interferon gamma, interleukin 6, interleukin 1 beta, and any combination thereof.

In another embodiment of the invention, a method for treating a patient suffering from renal disease includes administering to the patient effective amounts of antibodies, functional equivalents of antibodies or soluble cytokine receptors to at least two compounds selected from the group consisting of urea, creatinine, tumor necrosis factor alpha, interferon gamma, interleukin 6, and interleukin 1 beta.

In a further embodiment of the invention, a method for treating renal insufficiency or renal failure includes determining in a patient an elevated level of urea, creatinine or both and determining in the patient an elevated level of a cytokine selected from the group consisting of tumor necrosis factor alpha, interferon gamma, interleukin 6, and interleukin 1 beta. An antibody component is administered to the patient to reduce said elevated levels.

In yet another embodiment of the invention, a method for treating a patient suffering from renal disease includes administering to the patient an effective amount of antibody, or of a functional equivalent thereof, to a compound selected from the group consisting of urea, creatinine and any combination thereof, and an effective amount of antibody to a cytokine, an effective amount of a functional equivalent of the antibody, or an effective amount of a soluble receptor to the cytokine, or any combination thereof, wherein the cytokine is selected from the group consisting of tumor necrosis factor alpha, interferon gamma, interleukin 6, interleukin 1 beta, and any combination thereof.

In one aspect, the invention is directed to a method for treating a patient suffering from renal disease which includes administering to the patient an effective amount of a vaccine for producing endogenous antibody to a compound selected from the group consisting of urea, creatinine, or to a cytokine selected from the group consisting of tumor necrosis factor alpha, interferon gamma, interleukin 6, interleukin 1 beta, and any combination thereof.

In another aspect, the invention is directed to a method for treating a patient suffering from a renal disease and includes administering to the patient an effective amount of an antibody or of a functional equivalent thereof to urea, creatinine or a combination thereof.

In a further aspect, the invention is directed to a method for treating renal disease, the method including administering to a patient suffering from renal disease an effective amount of a functional equivalent of an antibody or of a soluble cytokine receptor to tumor necrosis factor alpha, interferon gamma, interleukin 6 or interleukin 1 beta.

In still another aspect, the invention is directed to a method for treating renal disease, wherein the method includes administering to a patient suffering from renal disease an effective amount of antibody to interleukin 6, interleukin 1 beta or any combination thereof.

The invention also is directed to a pharmaceutical composition and a method for its manufacture. The pharmaceutical composition includes effective amounts of antibody or a functional equivalent thereof to urea, creatinine, or both and of antibody, functional equivalent thereof or soluble cytokine receptor to tumor necrosis factor alpha, interferon gamma, interleukin 6, interleukin 1 beta or any combination thereof.

In a specific example, the pharmaceutical composition includes effective amounts of antibody to urea, creatinine, tumor necrosis factor alpha, interferon gamma, interleukin 6 and interleukin 1 beta. Functional equivalents of one or more antibodies or soluble cytokine receptors also can be employed.

In one aspect, a method for manufacturing a preferred pharmaceutical composition includes combining effective amounts of antibody, functional equivalent thereof or a soluble cytokine receptor to urea, creatinine, tumor necrosis factor alpha, interferon gamma, interleukin 6 and interleukin 1 beta.

In yet other aspects, the invention is directed to a kit, for instance a kit that includes an effective amount of antibody, or functional equivalent thereof, to a compound selected from the group consisting of urea, creatinine and any combination thereof and an effective amount of antibody, functional equivalent thereof, or a soluble cytokine receptor to a cytokine selected from the group consisting of tumor necrosis factor alpha, interferon gamma, interleukin 6, interleukin 1 beta, and any combination thereof.

In one example, the kit includes effective amounts of antibody, functional equivalent thereof or, if applicable, cytokine soluble receptor, to urea, creatinine, tumor necrosis factor alpha, interferon gamma, interleukin 6, and interleukin 1 beta.

The invention has several advantages. It is believed, for example, that the method of treatment can result in a reduction and possibly in the elimination of dialysis requirements and/or improvements in quality of life. The invention can provide for more pathogenetic treatment by removing hyperproduced cytokines and not just urinary retention products. Compared to dialysis, the method of treatment disclosed herein is more convenient and easier to provide. In some patients, the treatment described herein also may delay the onset of kidney failure.

Practicing the invention also allows customized treatment, depending on the specific cytokines that are elevated in a patient's circulation. Accordingly, a decrease in the incidence of side effects is expected.

The use of functional equivalents to the antibodies described herein can result in improvements in formulation and manufacturing, thereby reducing treatment costs. Functional equivalents also can be used to reduce or minimize side effects. Some of the advantages associated with the use of soluble cytokine receptors include specificity, high affinity and low immunogenicity.

In some aspects, the invention is particularly beneficial in managing ESRD patients who do not respond to erythropoietin therapy.

The above and other features of the invention including various novel details of construction and combinations of parts, and other advantages, will now be more particularly described and pointed out in the claims. It will be understood that the particular method and composition embodying the invention are shown by way of illustration and not as a limitation of the invention. The principles and features of this invention may be employed in various and numerous embodiments without departing from the scope of the invention.

DETAILED DESCRIPTION OF THE PREFERRED EMBODIMENTS

The invention generally relates to the treatment of renal disease and can be practiced in patients that include human as well as other mammalian subjects, for example, farm or wild animals, companion animals, laboratory or experimental animals, zoo animals, sports animals and others.

As used herein, the term "treatment" refers to an intervention performed in order to alter or prevent the development or pathology of a disorder or disease, for instance, to prevent or slow down the progression of a disease, or to lessen its severity. The term refers to both, therapeutic, as well as prophylactic or preventive measures.

As used herein, the term "renal disease" refers to acute or chronic renal failure, and other types of renal impairment or insufficiency as known in the medical arts. In some cases, the treatment is provided to a patient in an advanced stage of renal disease. In specific aspects of the invention, the treatment is provided as a supplement to dialysis. In other aspects, the treatment is provided as a partial or complete substitute to dialysis. The treatment also can be undertaken to delay the onset of kidney failure.

In addition to renal disease, the patient can also suffer from other diseases or underlying conditions such as diabetes, hypertension, shock, overwhelming infection, poisoning, heavy metal intoxication, cardiovascular abnormalities, endocrine, hormonal or metabolic disturbances and other medical problems. The treatment also can benefit patients exhibiting surgery-related complications affecting kidney function.

Candidates for the treatment disclosed herein can be selected based on clinical diagnosis, laboratory evaluations, or both.

In most patients with stable chronic renal disease (CRD), for example, the total body contents of $Na^+$ and $H_2O$ are increased modestly. The underlying etiologic disease process may itself disrupt glomerulotubular balance and promote $Na^+$ retention (e.g., glomerulonephritis), or excessive $Na^+$ ingestion may lead to cumulative positive $Na^+$ balance and attendant extracellular fluid volume (ECFV) expansion. Such ECFV expansion contributes to hypertension, which in turn accelerates further the progression of nephron injury. As long as water intake does not exceed the capacity for free water clearance, the ECFV expansion will be isotonic and the patient will remain normonatremic.

Hyponatremia is an uncommon complication in predialysis patients, and water restriction is only necessary when hyponatremia is documented. In the CRD patient who is not yet on dialysis but has clear evidence of ECFV expansion, administration of loop diuretics coupled with restriction of salt intake are the mainstays of therapy. The combination of loop diuretics with metalozone, which inhibits the $Na^{+}Cl^{-}$ cotransporter of the distal convoluted tubule, can sometimes overcome diuretic resistance. When the GFR falls to <5 to 10 mL/min per 1.73 $m^2$, even high doses of combination diuretics are ineffective. ECFV expansion under these circumstances usually means that dialysis is indicated.

In CRD, the decline in GFR is not necessarily accompanied by a concomitant and proportionate decline in urinary $K^+$ excretion. In addition, $K^+$ excretion in the gastrointestinal tract is augmented in patients with CRD. However, hyperkalemia may be precipitated in a number of clinical situations, including constipation, augmented dietary intake, protein catabolism, hemolysis, hemorrhage, transfusion of stored red blood cells, metabolic acidosis, and following the exposure to a variety of medications that inhibit $K^+$ entry into cells or $K^+$ secretion in the distal nephron. In addition, certain etiologies of CRD may be associated with earlier and more severe disruption of $K^+$ secretory mechanisms in the distal nephron, relative to the reduction in GFR. Most important are conditions associated with hyporeninemic hypoaldosteronism (e.g., diabetic nephropathy, etc.)

Acidosis is a common disturbance during the advanced stages of CRD. Although in a majority of patients with CRD the urine can be acidified normally, these patients have a reduced ability to produce ammonia. Hyperkalemia further depresses urinary ammonium excretion. The combination of hyperkalemia and hyperchloremic metabolic acidosis (known as type IV renal tubular acidosis, or hyporeninemic hypoaldosteronism) is most characteristically seen in patients with diabetes or in those with predominantly tubulointerstitial disease. Treatment of the hyperkalemia frequently improves the acidosis as well.

Adjustments in dietary intake and use of loop diuretics, occasionally in combination with metalozone, may be needed to maintain salt and hence extracellular fluid volume balance. Occasional patients with salt-wasting states need to be given sodium-rich diets or sodium supplements. Water restriction is indicated only if there is a demonstrated propensity to hyponatremia. Intractable ECFV expansion, despite dietary restriction and diuretic use, indicates the need to initiate renal replacement therapy. Hyperkalemia often responds to dietary restriction of potassium, avoidance of potassium-containing or -retaining medications, and to the use of diuretics if they are also indicated for management of sodium balance. Potassium-binding resins taken with cathartics can promote gastrointestinal potassium losses and thus are useful as temporizing measures in the treatment or avoidance of hyperkalemia in CRD patients. However, the need for such treatment over a prolonged period, in the absence of other reversible causes of hyperkalemia, usually signifies the need to initiate renal replacement therapy.

Patients with renal disease often exhibit elevated levels of non-protein nitrogen compounds. Urea, for example, is a waste product of protein metabolism and can be measured as blood urea nitrogen (BUN). In the course of renal disease, damaged kidneys generally are less able to clear urea from the blood stream and high BUN levels are observed.

Another non-protein nitrogen compound, creatinine, is a waste product formed in the enzymatic conversion of creatine by creatine amidohydrolase. As with BUN, patients having impaired renal function often exhibit increased creatinine serum concentrations.

Patient BUN and creatinine levels can be determined by routine laboratory procedures as known in the clinical or veterinary arts.

In many cases, renal disease, e.g., renal insufficiency or renal failure, also is associated with increased levels in at least one of tumor necrosis factor alpha (TNF-$\alpha$), interferon gamma (INF-$\gamma$), interleukin 6 (IL-6) or interleukin 1 beta (IL-1$\beta$). ESDR patients who do not respond to erythropoietin often exhibit high levels of interleukin 10 (IL-10) and/or interleukin 13 (IL-13).

Compounds such as TNF-$\alpha$, INF-$\gamma$, IL-6, and IL-1$\beta$ generally are referred to herein as "cytokines". Most cytokines are not produced constitutively, but transiently after stimulation and are not normally found in the serum in a bioactive form. Cytokines can play a role in the generation of an immune response and are intercellular mediators secreted by lymphocytes and/or macrophages and other cells. In turn, some cytokines such as, for instance, interferons, are capable of inducing other cytokines.

Cytokine levels can be measured, for example, by collecting a blood sample, separating plasma, for instance by centrifugation, and detecting cytokines, by a standard assay, e.g., enzyme linked immunosorbent assay (ELISA) and many other standard methods.

The presence of elevated levels of non-protein nitrogen compounds and/or cytokines can be established by comparing levels found in a patient with control levels, for instance with levels known to be present in normal subjects. In normal adult human subjects, for example, levels of creatinine generally are in the range of from about 0.8 to about 1.2 mg/dL and levels of urea nitrogen (BUN) in the range of from about 8 to about 21 mg/dL.

Levels of non-protein nitrogen compounds and/or cytokines can be measured and/or monitored prior to, during and after the treatment described herein.

In one example, the invention aims at reducing elevated levels of one or more non-protein nitrogen compound(s) and/or cytokine(s) in a patient suffering from renal disease through a treatment that includes antibodies, functional equivalents thereof, and, if applicable, soluble cytokine receptors. As used herein, the term "antibody component" refers to any combination of antibodies, functional equivalents thereof and, if applicable, one or more soluble cytokine receptors.

In a preferred aspect of the invention, the treatment includes antibody to at least two compounds selected from the group consisting of urea, creatinine, TNF-$\alpha$, INF-$\gamma$, IL-6, and IL-1$\beta$. Functional equivalents of antibodies as well as soluble cytokine receptors also can be employed. In another aspect, an antibody component includes a portion targeting one or more non-protein nitrogen compounds and another portion targeting a cytokine selected from the group consisting of TNF-$\alpha$, INF-$\gamma$, IL-6, IL-1$\beta$ and any combination thereof.

As used herein, the term "antibody" refers to monoclonal antibodies, polyclonal antibodies, multispecific antibodies, chimeric, human, including spontaneously produced antibodies derived from a subject's blood, humanized monoclonal and camelid antibodies.

Monoclonal antibodies are obtained from a population of substantially homogeneous antibodies, with individual antibodies being identical except for possible naturally-occurring mutations that may be present in minor amounts. Monoclonal antibodies are highly specific, being directed against a single antigenic site. In contrast to polyclonal antibody preparations, which include different antibodies directed against different determinants (epitopes), each monoclonal antibody is directed against a single determinant on the antigen. In addition to their specificity, monoclonal antibodies can be synthesized to be uncontaminated by other antibodies.

Chimeric antibodies are monoclonal antibodies in which a portion of the heavy and/or light chain is identical with or homologous to corresponding sequences of antibodies derived from a particular species or belonging to a particular antibody class or subclass, while the remainder of the chain(s) is identical with or homologous to corresponding sequences of antibodies derived from another species or belonging to another antibody class or subclass. See, e.g., U.S. Pat. No. 4,816,567 and Morrison et al., Proc. Natl. Acad. Sci. USA 81: 6851-6855 (1984).

Chimeric antibodies for use herein include primatized antibodies comprising variable domain antigen-binding sequences derived from a non-human primate (e.g., Old World Monkey, Ape, etc.), and human constant region sequences.

Humanized monoclonal antibodies are chimeric antibodies that contain minimal sequence derived from a non-human antibody. In many cases, humanized antibodies are human immunoglobulins (recipient antibody) in which residues from a hypervariable region of the recipient are replaced by residues from a hypervariable region of a non-human species (donor antibody) such as mouse, rat, rabbit or non-human primate, having the desired antibody specificity, affinity, and capability. In some cases, framework region (FR) residues of the human immunoglobulin are replaced by corresponding non-human residues. Humanized antibodies may also comprise residues that are not found in the recipient antibody or in the donor antibody. These modifications can further refine antibody performance. A humanized antibody optionally can also comprise at least a portion of an immunoglobulin constant region (Fc), typically that of a human immunoglobulin. Further details are described by Jones et al., Nature 321:522-525 (1986); Riechmann et al., Nature 332:323-329 (1988); and Presta, Curr. Op. Struct. Biol. 2:593-596 (1992).

Other suitable antibodies for use in the treatment disclosed herein are camelid antibodies, derived from camelid species. Camelid antibodies differ from those of most other mammals in that they lack a light chain, and thus comprise only heavy chains with complete and diverse antigen binding capabilities (Hamers-Casterman et al., 1993, Nature, 363:446-448). Such heavy-chain antibodies tend to be smaller than conventional mammalian antibodies, often are more soluble than conventional antibodies, and further demonstrate an increased stability compared to some other antibodies.

Camelid species include, but are not limited to Old World camelids, such as two-humped camels (*C. bactrianus*) and one humped camels (*C. dromedarius*). The camelid family further includes New World camelids including, but not limited to llamas, alpacas, vicuna and guanaco. Camelid species for the production of antibodies and for other uses are available from various sources, including but not limited to, Camello Fataga S. L. (Gran Canaria, Canary Islands) for Old World camelids, and High Acres Llamas (Fredricksburg, Tex.) for New World camelids.

Multispecific antibodies can be specific to different epitopes of a single molecule or can be specific to epitopes on different molecules. Such antibodies can be monospecific, bispecific, trispecific or can have greater multispecificity. Methods for designing multispecific antibodies are known in the art. See, e.g., Millstein et al. (1983) Nature 305:537-539; Kostelny et al. (1992) J. Immunol. 148:1547-1553; WO 93/17715.

Antibodies and antibody production are further described, for instance, by Harlow et al., 1999, "Using Antibodies: A Laboratory Manual", Cold Spring Harbor Laboratory Press, NY; Harlow et al., 1989, "Antibodies: A Laboratory Manual", Cold Spring Harbor, N.Y.; Houston et al., 1988, Proc. Natl. Acad. Sci. USA 85:5879-5883; Bird et al., 1988, Science 242:423-426).

To produce antibodies suitable for use in the present invention, a cytokine or antigen may be modified or administered in an adjuvant in order to increase the peptide antigenicity. Methods of increasing the antigenicity of a polypeptide are known in the art. Such procedures include coupling the antigen with a heterologous protein (such as globulin or β-galactosidase) or through the inclusion of an adjuvant during immunization.

Antibodies suitable in the treatment disclosed herein also can be antibodies that are spontaneously produced by a subject. For example, it can be determined by laboratory testing that a patient suffering from renal disease produces antibodies to one or more of urea, creatinine, TNF-α, INF-γ, IL-6, or IL-1β. The antibodies can be isolated from the patient's blood and used in treating the patient. Procedures for separating endogenously produced antibodies from a subject's blood are known in the art. Patient's plasma is fractionated by ethanol precipitation of the proteins according to Cohn Method 6 and Oncley Method 9, and the immunoglobulin is purified. Each milliliter contains 50±10 mg immunoglobulin, primarily IgG, and trace amounts of IgA and IgM; 50 mg sucrose; and 10 mg Albumin (Human). The sodium content is 20-30 mEq per liter, i.e., 0.4-0.6 mEq per 20 mL or 1.0-1.5 mEq per 50 mL.

Several techniques for preparing monoclonal antibodies are known in the art (Campbell, A. M., "Monoclonal Antibody Technology: Laboratory Techniques in Biochemistry and Molecular Biology," Elsevier Science Publishers, Amsterdam, The Netherlands (1984); St. Groth et al, J. Immunol. Methods 35:1-21 (1980). For example, in one embodiment an antibody capable of binding to INF-γ is generated by immunizing an animal with natural, synthetic or recombinant INF-γ.

Monoclonal antibodies can be prepared, for instance, by a hybridoma methodology such as described by Kohler et al., Nature 256: 495 (1975), or they may be produced using recombinant DNA methods in bacterial or eukaryotic animal or plant cells (see, e.g., U.S. Pat. No. 4,816,567). Monoclonal antibodies can also be isolated from phage antibody libraries using, for instance, the techniques described in Clackson et al., Nature 352: 624-628 (1991) and Marks et al., J. Mol. Biol. 222: 581-597 (1991).

For example, spleen cells from the immunized animals are removed, fused with myeloma cells, such as SP210-Ag14 myeloma cells, and allowed to become monoclonal antibody producing hybridoma cells. A hybridoma is an immortalized cell line which is capable of secreting a specific monoclonal antibody. Any one of a number of methods known in the art can be used to identify the hybridoma cell which produces an antibody with the desired characteristics. These include screening the hybridomas with an ELISA assay, western blot analysis, or radioimmunoassay (Lutz et al., Exp. Cell Res. 175:109-124 (1988)). Hybridomas secreting the desired antibodies are cloned and the class and subclass are determined using procedures known in the art. See, e.g., "Monoclonal Antibody Technology: Laboratory Techniques in Biochemistry and Molecular Biology", supra).

For polyclonal antibodies, antibody-containing antiserum is isolated from the immunized animal and is screened for the presence of antibodies with the desired specificity using one of the above-described procedures. Polyclonal antibodies raised from animals immunized with specific antigens (IFNs, TNF, etc.) can be used after the isolation of the active fraction (e.g., IgG) or isolated Fab fragment.

In a specific example, the production is that of polyclonal sera from camelid species. The production method is similar to the production of polyclonal sera from other animals such as sheep, donkeys, goats, horses, mice, chickens, rats, and the like. Isolation of camelid antibodies from the serum of a camelid species can be performed by many methods known in the art, including but not limited to ammonium sulfate precipitation, antigen affinity purification, Protein A and Protein G purification, and the like.

A camelid species can be immunized with a desired antigen, for example IFN-γ, IL-1, a TNF-α peptide, or fragment thereof, using techniques known in the art. The whole blood can then be drawn from the camelid and sera can be separated using standard techniques. The sera can then be absorbed onto a Protein G-Sepharose column (Pharmacia, Piscataway, N.J.) and washed with appropriate buffers, for example 20 mM phosphate buffer (pH 7.0). The camelid antibody can then be eluted using a variety of techniques known in the art, for example 0.15M NaCl, 0.58% acetic acid (pH 3.5). The efficiency of the elution and purification of the camelid antibody can be determined by various methods, including SDS-PAGE, Bradford Assays, and the like. The fraction that is not absorbed can be bound to a Protein A-Sepharose column (Pharmacia, Piscataway, N.J.) and eluted using, for example, 0.15M NaCl, 0.58% acetic acid (pH 4.5).

In addition, camelid antibodies can be expressed from nucleic acid, by methods known in the art, as described, for instance, in U.S. Pat. Nos. 5,800,988; 5,759,808; 5,840,526, and 6,015,695. Briefly, cDNA can be synthesized from camelid spleen mRNA. Isolation of RNA can be performed using methods and compositions, such as TRIZOL (Gibco/BRL, La Jolla, Calif.). Total RNA can be isolated from tissues using the guanidium isothiocyanate method detailed in, for example, Sambrook et al. (1989, "Molecular Cloning, A Laboratory Manual", Cold Spring Harbor, N.Y.). Methods for purification of mRNA from total cellular or tissue RNA are known in the art, and include, for example, oligo-T paramagnetic beads. cDNA synthesis can then be obtained from mRNA using mRNA template, an oligo dT primer and a reverse transcriptase enzyme, available commercially from a variety of sources, including Invitrogen (La Jolla, Calif.). Second strand cDNA can be obtained from mRNA using RNAse H and *E. coli* DNA polymerase I, according to techniques known in the art.

Antibodies also can be produced using polyclonal antibody libraries, such as described, for instance, in U.S. Pat. No. 6,335,163, issued to Sharon on Jan. 1, 2002, the teachings of which are incorporated herein by reference in their entirety. Further techniques that can be used are described in International Patent Application Publication No. WO 2004061104, "Method for Manufacturing Recombinant Polyclonal Proteins", published on Jul. 22, 2004 and International Patent Application Publication No. WO 2005042774, "Method for Linking Sequences of Interest", published on May 12, 2005. The teachings of both international publications are incorporated herein by reference in their entirety.

In specific examples, antibodies are prepared using Symphage™, a phage display technology for generating and screening libraries for recombinant polyclonal antibodies, available from Symphogen A/S, Denmark. Other techniques available from Symphogen A/S, that can be employed include: Sympress™, a manufacturing technology for the production of a recombinant polyclonal antibody (rpAb) in a single bioreactor. The rpAb constitute a large diversity of individual antibody members (produced in the same bioreactor), a diversity which is maintained from batch to batch; and Symplex™, a technique for high throughput isolation of original pairs of antibody heavy and light chain variable region genes from human donor blood.

In further aspects of the invention, antibodies are produced endogenously by an "immunization" procedure whereby administration of a 'vaccine", e.g., an antigen, elicits an antibody response to the antigen. For example, the use of an anti-interferon-alpha vaccine, specifically inactivated recombinant IFN-alpha-2b, aimed at counteracting overproduction of IFN-alpha in AIDS patients is described, for example, by A. Gringeri et al. in the article with the title "Absence of Clinical, Virological, and Immunological Signs of Progression in HIV-1-Infected Patients Receiving Active Anti-Interferon-alpha Immunization: a 30-Month Follow-Up Report", *J. Acquir. Immune Defic. Syndr. Hum. Retrovirol.*, 13(1), pp 55-67 (1996).

The treatment disclosed herein also can be practiced using one or more "functional equivalent(s)" of an antibody. Such a functional equivalent is capable of specifically binding to, or destroying, the same antigenic determinant as the antibody, thereby neutralizing the molecule, e.g., antibody-like molecules, such as single chain antigen binding molecules. Functional equivalents of an antibody include antibody fragments, antibody variants, antibody derivatives and/or antibody analogs that exhibit the desired biological activity.

The phrase "fragment" or "analog" of an antibody refers to a compound having qualitative biological activity in common with the full-length antibody.

The term "antibody mutant" refers to an amino acid sequence variant of an antibody wherein one or more of the amino acid residues have been modified. Such mutants necessarily have less than 100% sequence identity or similarity (homology) with the amino acid sequence having at least about 75% amino acid sequence identity with the amino acid sequence of either the heavy or light chain variable domain of the antibody, alternatively at least about 80% amino acid sequence identity, alternatively at least about 85% amino acid sequence identity, alternatively at least about 90% amino acid sequence identity, alternatively at least about 95% amino acid sequence identity or alternatively at least about 96%, 97%, 98% or 99% amino acid sequence identity.

As used herein, the phrase "biologically active fragment" refers to a part of the complete molecule which retains all or some of the catalytic or biological activity possessed by the complete molecule, especially activity that allows specific binding of the antibody to an antigenic determinant.

The term "analog" refers to peptides, and in particular polypeptides, derivatives, allelic or species variants that have the desired biological activity. The peptides and polypeptides act on the same target as antibodies and can be used to inhibit binding of a cytokine to its receptor. A "variant" or "allelic or species variant" of a protein refers to a molecule substantially similar in structure and biological activity to the protein. Thus, if two molecules possess a common activity and may substitute for each other, it is intended that they are "variants," even if the composition or secondary, tertiary, or quaternary structure of one of the molecules is not identical to that found in the other, or if the amino acid or nucleotide sequence is not identical.

The term "derivative" includes functional and chemical derivatives, for instance fragments, segments, variants or analogs of a molecule. A molecule is a "chemical derivative" of another, if it contains additional chemical moieties not normally a part of the molecule. Such moieties may improve the molecule's solubility, absorption, biological half life, and the like, or they may decrease toxicity of the molecule, eliminate or attenuate undesirable side effects of the molecule, and the like. Moieties capable of mediating such effects are disclosed in Remington's Pharmaceutical Sciences (1980). Procedures for coupling such moieties to a molecule are well known in the art.

As used herein, the term "functional equivalent" of an antibody also refers to enzymes that act on the same target as antibodies.

Functional equivalents such as, for instance, antibody fragments, can be identified using phage display techniques combined with synthetic libraries.

Soluble cytokine receptors are known to regulate inflammatory or immune events and are believed to function as agonists or antagonists of cytokine signaling. Receptors that bind cytokines are typically composed of one or more integral membrane proteins that bind the cytokine with high affinity and transduce this binding event to the cell through the cytoplasmic portions of the certain receptor subunits. Cytokine receptors have been grouped into several classes on the basis of similarities in their extracellular ligand binding domains. For example, the receptor chains responsible for binding and/or transducing the effect of interferons are members of the class II cytokine receptor family, based upon a characteristic 200 residue extracellular domain.

In some examples, the treatment is practiced using a combination of different types of antibody or equivalents thereof targeting the same compound, e.g., a cytokine. For instance, the treatment can employ a mixture of a monoclonal antibody targeting INF-γ as well as a biologically active fragment of an antibody also targeting INF-γ. In other examples, the treatment includes a monoclonal antibody targeting INF-γ, a biologically active fragment of an antibody also targeting INF-γ as well as a soluble INF-γ receptor.

In preferred aspects of the invention, the treatment employs a combination or antibodies, preferably targeting those compounds found at elevated levels in patients suffering from renal disease. A patient can receive an antibody to a non-protein nitrogen compound in combination with an antibody to a cytokine. More specifically, an antibody or its functional equivalent targeting at least one non-protein nitrogen compound, e.g., urea and/or creatinine, can be combined with one and preferably more than one antibody, its/their functional equivalent(s) and/or one or more soluble cytokine receptor(s) targeting at least one cytokine selected from TNF-α, INF-γ, IL-6, and IL-1β.

A combination that includes antibodies to both creatinine and urea, together with antibodies targeting TNF-α, INF-γ, IL-6 and IL-1β is preferred. Functional equivalents of the antibodies and/or soluble receptors to the cytokines also can be employed.

Specific antibodies, functional equivalents of antibodies and soluble cytokine receptors suitable for practicing the invention are further discussed below.

Both creatinine and urea are haptens and they can be bound to a protein carrier (e.g., gelatine). Methods of binding haptens with carrier proteins are described, for example, by Obermeier F & Pick E. Wein Klin Wschr., 1903, Bd 16, S. 659-7; and Idem Ibid 1904 Bd 17, S. 265. In other examples, the amino acid valine has been used as a coupling agent between a carrier protein and a hapten, as described by Kaverzneva E & Kiseleva V. Biochemistry, 1966, 6, p 204; Skurkovich S & Milonova T. Journal of Microbiology, Epidemiology & Immunolgy, 1974, 1, p 89.

Several antibodies to urea and/or creatinine have been developed specifically for laboratory assays designed to detect creatinine and/or urea in serum samples. A creatinine-specific antibody is described, for example, in U.S. Pat. No. 4,485,177 issued on Nov. 27, 1984, and U.S. Pat. No. 4,578,361, issued on Mar. 25, 1986, both to Siedel et al; the teachings of U.S. Pat. Nos. 4,485,177 and 4,578,361 are incorporated herein by reference in their entirety. This creatinine specific antibody forms a hapten-antibody complex with creatinine and can be prepared by raising an antiserum with a conjugate of creatinine and a protein suitable for antiserum formation, connected via an aliphatic or araliphatic carboxylic bridge member.

Creatinine-specific antibodies have been generated and used for highly sensitive and specific immunochemical creatinine determinations. Creatinine was derivatized at N3 and coupled to KLH carrier protein. On the basis of this immunogen, monoclonal antibodies were developed by hybridoma technology. Antibodies from various clones have been characterized with BIAcore 2000 with respect to the dissociation constant and specificity. Antibodies of clone B90-AH5 exhibited the lowest dissociation constant (0.74 microM) and the highest specificity for creatinine, as described by Benkert A, Scheller F, Schossler W, Hentschel C, Micheel B, Behrsing O, Scharte G, Stocklein W, Warsinke A., "Development of a Creatinine ELISA and an Amperometric Antibody-Based Creatine Sensor with a Detection Limit in the Nanomolar Range", *Anal Chem.* 2000 Mar. 1; 72(5):916-21.

Antibodies targeting urea are described by Rohde M, Schenk J A, Heymann S, Behrsing O, Scharte G, Kempter G, Woller J, Hohne W E, Warsinke A, Micheel B., in an article entitled "Production and Characterization of Monoclonal Antibodies Against Urea Derivatives", *Appl Biochem Biotechnol*., October 1998; 75(1), pp. 129-37. A panel of monoclonal antibodies was generated against the urea-based hapten N-(2-N-chloroacetylaminobenzyl)-N'-4-chlorophenylurea as a tool for building up sensitive immune assays to detect urea derivatives and to screen them for catalytic antibodies (Abs). Eleven hybridomas were obtained that produced Abs reactive to the hapten. All Abs were of IgG class. Cross reactivities of the Abs to different haptens were examined, especially to a possible transition-state analog and four of the hybridomas, namely R2-DA10/F7, R2-GE7/H2, R2-HC2/A5, R2-HD6/F7, produced Abs crossreactive with the transition-state analog. From the 11 hybridomas, hybridoma B76-BF5 was chosen for further characterization. Compared to the other Abs, B76-BF5 showed the strongest binding and had a rather restricted specificity.

Polyclonal antibodies targeting TNF-α can be obtained by immunizing goats, or other animals, with recombinant human TNF-α ("r-Hu-TNF-α"), and isolating the IgG from the animals, as described, for example in U.S. Pat. No. 6,333,032, issued to Skurkovich et al. on Dec. 25, 2001, the teachings of which are incorporated herein by reference in their entirety.

Examples of other suitable antibodies targeting TNF-α include but are not limited to those currently known in the clinical and medical arts, such as, for example, a chimeric human-mouse monoclonal IgG1 antibody directed against TNF-α, developed by Centocor and known clinically as infliximab (Remicade™), and a fully human antibody directed against TNF-α, developed by Abbott and known clinically as adelimumab (Humira™).

An example of a functional equivalent of an antibody targeting TNF-α is anti-TNF-α antibody fragment labeled CDP 870, from Celltech Group plc, UK. CDP 870 has been reported in Phase III clinical trials in Europe for rheumatoid arthritis and Crohn's disease.

An example of a vaccine directed against autologous TNF-α was reported by A. M. Waterson et al. in an article with the title "Phase I Study of TNFalpha AutoVaccine in Patients with Metastatic Cancer", Cancer Immunol. Immunother. 54(9), pp. 848-57 (2005). The vaccine used consisted of two recombinant TNF-α proteins, with specific peptides replaced by foreign immunodominant T cell epitopes from tetanus toxoid.

Receptors to TNF and their use are described, for instance, in U.S. Pat. Nos. 5,395,760; 5,945,397; 6,201,105; 6,572,852, to Smith et al. and U.S. Pat. No. 5,605,690 to Jacobs et al., the teachings of which are incorporated herein by reference in their entirety.

A specific example of a soluble receptor binding to TNF-α is a dimeric fusion protein consisting of the extracellular ligand-binding portion of the human 75 kilodalton (p75) TNF receptor linked to the Fc portion of human IgG1. It is known clinically as etenercept (Enbrel™). Initially developed by Immunex, Enbrel™ can be currently obtained from Amgen.

Antibodies that can be used to target human INF-γ are disclosed, for instance, in U.S. Pat. No. 6,333,032, issued to Skurkovich et al. on Dec. 25, 2001.

To prepare the anti-INF-γ antibody, adult rabbits are immunized with a purified INF-γ in a fluid medium, including, e.g., Freund's adjuvant. For an initial period, the rabbits receive several subcutaneous injections, for instance at day 1, 4, 14, and 43. Once monthly injections are then administered for the following several months, e.g., six months. The serum is drawn from the rabbits when the desired titer is reached and is used to isolate and purify IgG. In addition, polyclonal antibodies targeting INF-γ can be obtained, for example, by immunizing goats with r-Hu IFN-γ and isolating the IgG from the animals.

Fontolizumab (HuZAF™) also can be employed. HuZAF™ is a humanized monoclonal antibody that binds to IFN-γ. It is made by Protein Design Labs and is being investigated in Crohn's disease.

Examples of polypeptides that can be used to inhibit the binding of human INF-γ to cellular receptors and the biological activity of INF-γ are described in U.S. Pat. No. 5,451,658, "Antagonists of Human Gamma Interferon", issued to Seelig on Sep. 19, 1995, the teachings of which are incorporated herein by reference in their entirety. Some of the antagonists described bind to specific regions of gamma interferon which are believed to be involved in interactions between the interferon and its receptors. Other antibody antagonists are anti-idiotypic antibodies which appear to compete directly with gamma interferon for binding to the cellular receptors.

An example of a soluble interferon-gamma receptor fragment and techniques for obtaining it are described in U.S. Pat. No. 5,578,707, "Soluble Interferon-Gamma Receptor Fragment", issued to Novick et al. on Nov. 26, 1996, the teachings of which are incorporated herein by reference in their entirety.

Examples of polyclonal or monoclonal anti-IL-6 antibodies include those available, for instance, from R&D Systems, Inc. of Minneapolis, Minn., such as monoclonal and/or polyclonal antibodies targeting human, canine, porcine or equine IL-6.

Human, feline and other polyclonal and/or monoclonal anti-IL-1β antibodies are available commercially from R&D Systems, Inc. of Minneapolis, Minn. A functional equivalent, a PEGylated anti-IL-1β antibody fragment, labeled CDP 484 (Celltech Group, PLC, UK) has been reported in preclinical trials for inflammatory disease.

The antibodies, their functional equivalent(s), and/or soluble cytokine receptors preferably are provided according to an administration route, schedule and dosage regiment suitable to the patient being treated, the severity of elevated levels, other underlying conditions, synergistic effects, the specific formulation, drug bioavailability curves, presence and/or severity of adverse reactions and other factors known in the medical and pharmaceutical arts.

The antibodies or functional equivalents described herein can be administered parenterally or by other routes. Specific examples of suitable administration routes include but are not limited to intravenous, intramuscular, subcutaneous, intranasal, ocular, pulmonary, vaginal, rectal, transdermal, oral and others known in the art.

The entire antibody component can be administered by a single route, using, for instance a composition such as the one described below. In other aspects of the invention, different routes are employed to deliver the antibodies or their functional equivalents. For instance, an antibody to creatinine can be administered by a route that is different from that used to deliver one or more of the antibodies targeting cytokines.

In one embodiment the entire antibody component is administered at the same time. Administration can be daily or can be at higher or lower frequency. In specific examples the antibody component is administered 1 to 3 times a week The administration of some of the antibodies, equivalents thereof or soluble cytokine receptors also can be staggered with respect to that of others. For instance, a patient can receive a functional equivalent to INF-γ two or three times a week, and antibodies to creatinine and to urea, both of which can be administered once daily or simultaneously or at twelve hours intervals of one another.

In many cases, the antibody component is administered in conjunction with a dialysis regimen. For a majority of patients with chronic renal failure, between 9 and 12 h of dialysis is required each week, usually divided into three equal sessions. However, the dialysis dose must be individualized. Recently there has been much interest in the possibility that more frequent dialysis may be associated with improved outcomes in patients with acute or chronic renal failure.

In a preferred aspect of the invention, administering the antibody component results in essentially eliminating the need for dialysis. Thus, administering an antibody component two or three times per week can lead to either no need of dialysis or making it necessary on an infrequent basis, such as once every two to four weeks.

In another aspect of the invention, administration of the antibody component results in a decrease in dialysis frequency. Thus, administering antibody component once weekly can lead to decreasing dialysis frequency to once or twice per week.

In a further aspect of the invention, administration of the antibody component is tailored to increase or maximize the beneficial effects of dialysis. In one example, a patient undergoing dialysis on a schedule of three times per week, receives the entire antibody component on a schedule of once per week.

Without wishing to be bound by a particular mechanism or interpretation of the invention, it is believed that one of the reasons for continuing to administer dialysis is to address accumulation of potassium and development of metabolic acidosis. However, even if dialysis is continued, it is believed that administering the antibody component, as described herein, results in a reduction in dialysis frequency.

The methods and compositions described herein preferably provide the antibodies, their functional equivalents or soluble cytokine receptors in effective amounts. As used herein, the term "effective amount" refers to an amount effective at dosages and for periods of time necessary to achieve the desired therapeutic or prophylactic result. For instance, the desired result may be to reduce the level of a non-protein nitrogen compound or a cytokine, e.g., IL-6 by at least 50%. Preferably, the desired result is to reduce the level by at least 80%. In most preferred cases, the desired result is a level within a normal range for that compound.

A "therapeutically effective amount" may vary according to factors such as the stage of the disease, age, sex, and weight of the individual, and the ability of the antibody to elicit a desired response in the individual.

A "prophylactically effective amount" refers to an amount effective at dosages and for periods of time necessary to achieve the desired prophylactic result. Since a prophylactic dose is used in subjects prior to or at an earlier stage of disease, the prophylactically effective amount often is less than the therapeutically effective amount.

Synergistic effects can result in lower effective amounts being administered. Such effects can be obtained by a specific combination of antibodies targeting one or more compounds selected from urea, creatinine and cytokines. Synergistic effects also can be observed with the use of adjuvants and/or other compounds.

Homeopathic approaches also can be employed and the invention can be carried out using effective amounts that encompass amounts established by homeopathic practices.

An effective amount of an antibody, functional equivalent thereof or soluble cytokine receptor is that amount which is effective, upon single or multiple dose administration to a patient, to bind to, neutralize or inhibit at least a portion of the compound, e.g., urea, creatinine and/or, cytokine, causing, directly or indirectly, the high levels observed in the patient suffering from renal disease. In preferred embodiments, the effective amount is that amount which is effective, upon single or multiple dose administration to a patient, to bring non-nitrogen compounds and/or cytokine levels to within a normal range.

For example, the effect of administering an effective amount of antibody to TNF-α, IFN-γ, IL-6 and/or IL-1β to a patient suffering from renal failure results in lowering the levels of these compounds. The reduction can be quantitatively determined in terms of reduced fluid activity level of one or more of the elevated cytokines, i.e., TNF-α, IFN-γ, IL-6 and/or IL-1β, or all four. The lowering of the cytokine activity level may be measured directly in the treated patient, or the reduction in cytokine activity level may be projected from clinical studies in which dose regimens useful in achieving such reduction are established.

An effective amount of the antibody, its functional equivalent or soluble cytokine receptor can be determined by the use of known techniques and/or by observing results obtained under analogous circumstances.

In determining dosage, a number of factors are considered, including, but not limited to: the species of mammal; its size, age, and general health; the specific disease involved; the degree of or involvement or the severity of the disease; the response of the individual patient; route of administration and desired schedule; bioavailability characteristics of the preparation being administered; the use of concomitant medication; and other relevant circumstances.

In oral administration, the dose of one antibody or functional equivalent thereof can be in the range of from about 0.1 to about 10.0 mg/kg patient body weight per day. For injectable formulations a suitable starting dose may be around 0.1 mg/kg patient body weight per day. The dose may be increased or decreased depending on factors such as response to treatment, patient tolerance and so forth.

The antibodies, their functional equivalents and/or soluble cytokine receptors can be formulated as a pharmaceutical composition. The pharmaceutical composition can consist essentially of the antibody component or can include additional ingredients, as further described below.

A portion of the antibody component includes an antibody or a functional equivalent thereof to urea, creatinine or both. Another portion of the antibody component includes an antibody, a functional equivalent thereof or a soluble cytokine receptor to TNF-α, INF-γ, IL-6 and IL-1β.

In a preferred embodiment, the antibody component targets urea, creatinine, TNF-α, INF-γ, IL-6 and IL-1β. Effective amounts are preferred.

As an illustrative example, a suitable antibody component can include antibodies to urea, creatinine, IFN-γ and IL-6, a soluble receptor to TNF-α, and a functional equivalent of an antibody to IL-1β, e.g., an antibody fragment.

The pharmaceutical composition that consists essentially of or that includes the antibody component can be prepared as a solution, can be lyophilized, or dried. The composition can be provided in gels, solutions, suspensions, emulsions, microemulsions, high viscosity fluids, syrups, chewing gum, nanoparticles, powders, caplets, tablets, suppositories, enemas, injections, infusions, inhalation formulations, e.g., aerosols or powders, and so forth.

The pharmaceutical composition can include additives, for example carriers, excipients, adjuvants, stabilizers and others. Physiologically acceptable compounds are preferred. The additives can be a solid, semi-solid, or liquid materials which can serve as a vehicle or medium for the active ingredient(s). Examples of suitable carriers, excipients, or stabilizers include but are not limited to buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Other materials that can be employed include, for instance, binders such as microcrystalline cellulose, starch paste, gum tragacanth or gelatin; excipients such as starch or lactose, disintegrating agents such as alginic acid, corn starch and the like; lubricants such as magnesium stearate; glidants such as colloidal silicon dioxide; sweetening agents such as sucrose or saccharin may be added, or a flavoring agent such as peppermint, methyl salicylate or orange flavoring, of the types usually used in the manufacture of medical preparations; coatings such as sugar, shellac, or other enteric coating agents; dyes and coloring agents; diluents, sterile solutions or normal saline; and other materials.

The proportion and nature of carriers, excipients, adjuvants, stabilizers, etc. can be determined by the solubility and chemical properties of the compound selected, the chosen route of administration, and standard pharmaceutical practice.

The pharmaceutical composition can have sustained-release properties. Suitable examples of sustained-release preparations include semipermeable matrices of solid hydrophobic polymers containing the antibody component, which matrices are in the form of shaped articles, e.g., films, patches, microcapsules and so forth.

Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release active ingredients for shorter time periods.

When encapsulated antibodies remain in the body for a long time, they may denature or aggregate as a result of exposure to moisture at 37° C. Rational strategies can be devised for stabilization depending on the mechanism involved. For example, if the aggregation mechanism is discovered to be intermolecular S—S bond formation through thiodisulfide interchange, stabilization may be achieved by modifying sulfhydryl residues, lyophilizing from acidic solutions, controlling moisture content, using appropriate additives, and developing specific polymer matrix compositions.

Optionally, the pharmaceutical composition can include other active ingredients such as erythropoietin, vitamins, pain killers, antibiotics, antiviral and other drugs, steroids, potassium blockers, anti-acidosis compounds, and so forth.

In a specific example, the antibody component is added to a formulation suitable for supplying subcutaneous fluids to a veterinary subject such as a cat or dog suffering from chronic renal failure. In other examples, the pharmaceutical composition includes a drug that reduces a cytokine level, such as, for instance, pentoxyfilline.

Preferably, the antibody component is present in the composition in an amount in the range of from about 10 to about 99% by weight of the pharmaceutical composition. The amount may depend upon the particular type of formulation and preferably is such that a suitable dosage will be obtained. The amount of antibody component present in a composition, e.g., a caplet, tablet, powder, gel or solution can be determined by a suitable assay such as ELISA or by other techniques.

The pharmaceutical composition can be prepared by combining antibodies, functional equivalents of antibodies and/or soluble cytokine receptors in one formulation. The process is not limited to any particular order of adding ingredients. One or more ingredients can be added simultaneously and sequential additions also can be carried out. Laboratory, pilot plant and commercial operations can be employed. Mixing, spray drying, emulsifying, purifying, compounding, and many other additional steps known in the fields of drug synthesis and manufacture also can be used to produce the composition.

One or more of the antibodies discussed herein, equivalents thereof, or soluble cytokine receptors can be provided in a kit. In one example, the entire antibody component is present in the kit in one composition, e.g., as gel caplets. The antibody component can be present in a pharmaceutical composition and in amounts such as described above. The kit can include the antibody component to be administered, arranged according to an administration schedule. Thus tablets or caplets can be provided in blisters or pouches arranged on one or more sheets, with rows and columns labeled to facilitate tracking a desired administration schedule.

In other examples, the kit includes separate antibodies, functional equivalents thereof, and/or soluble cytokine receptors to at least some of urea, creatinine, TNF-α, INF-γ, IL-6 and IL-1β Color coding and/or text can be employed to distinguish antibodies specific to each of the non-protein nitrogen compound(s) and/or cytokine(s) being targeted.

The kit can further comprise an applicator, for example, a pipette, a syringe, a dropper, a spray, an inhaler, a nebulizer, enema equipment and others known in the art.

Instructional materials describing the antibody component, methods for using the applicator, possible adverse reactions, and other information also can be included in the kit.

The invention is further illustrated by the following examples, which are not intended to be limiting.

EXEMPLIFICATION

Example 1

A 13 year old male cat with chronic renal failure and receiving subcutaneous Lactated Ringer's Injection fluid twice weekly, has a BUN level of 49 mg/dL (normal range 15-34 mg/dL) and a creatinine level of 2.5 mg/dL (normal level 0.8-2.3 mg/dL).

The cat receives antibody to creatinine and to urea on an initial schedule designed to reduce these non-protein nitrogen compounds to normal levels.

Example 2

A 16 and ½ year old female cat with a history of chronic renal failure for a documented period of one year is diagnosed with hyperthyroidism. The laboratory values are BUN: 45 mg/dL (normal range 15-34 mg/dL); creatinine 2.2 mg/dL (normal range 0.8-2.3 mg/dL); and T-4: 5.5 ng/dL (reference range 1.2-4.3 ng/dL). Based on the newly diagnosed hyperthyroidism and the known history of kidney failure, the cat receives 5 mg methimazole once daily in combination with antibodies to both BUN and creatinine on an administration regimen designed to reduce BUN values to normal levels.

Example 3

A human patient receiving dialysis 3 times a week, has creatinine level of 8 mg/dL and BUN level of 60 mg/dL. The patient also presents with elevated levels of IFN-gamma, TNF-alpha and IL-6. The following antibodies are administered: anti-creatinine, anti-urea, anti-IFN-gamma, anti-TNF-alpha and anti-IL-6.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for treating a patient suffering from chronic renal failure, associated with elevated levels of one or more of tumor necrosis factor alpha, interferon gamma or interleukin 6, the method comprising administering to the patient a soluble cytokine receptor to the one or more of tumor necrosis factor alpha, interferon gamma or interleukin 6, wherein the soluble cytokine receptor is administered in an amount effective to reduce levels of the one or more of tumor necrosis factor alpha, interferon gamma or interleukin 6.

2. A method for treating a patient suffering from chronic renal failure, associated with elevated levels of interleukin-6, interleukin 1 beta or both, the method comprising administering to the patient antibodies to interleukin 6, antibodies to interleukin 1 beta, or antibodies to interleukin 6 and antibodies to interleukin 1 beta, wherein the antibodies are administered in an amount effective to reduce levels of interleukin-6, interleukin 1 beta or both.

3. The method of claim 1, wherein the patient is selected from a group of patients receiving dialysis according to a dialysis regimen.

4. The method of claim 2, wherein the patient is selected from a group of patients receiving dialysis according to a dialysis regimen.

* * * * *